United States Patent
Kraft et al.

(10) Patent No.: US 11,701,649 B2
(45) Date of Patent: Jul. 18, 2023

(54) PROCESS FOR REGENERATION OF HYDROGENATION CATALYSTS

(71) Applicant: Evonik Operations GmbH, Essen (DE)

(72) Inventors: Johannes Kraft, Niederkassel (DE); Lena Altmann, Dorsten (DE); Johan Anton, Dorsten (DE); Michael Grass, Haltern am See (DE)

(73) Assignee: Evonik Operations GmbH, Essen (DE)

( * ) Notice: Subject to any disclaimer, the term of this patent is extended or adjusted under 35 U.S.C. 154(b) by 7 days.

(21) Appl. No.: 17/543,261

(22) Filed: Dec. 6, 2021

(65) Prior Publication Data

US 2022/0193652 A1    Jun. 23, 2022

(30) Foreign Application Priority Data

Dec. 18, 2020 (EP) .................................. 20215551

(51) Int. Cl.
| | | |
|---|---|---|
| *B01J 38/04* | (2006.01) | |
| *B01J 21/06* | (2006.01) | |
| *B01J 23/46* | (2006.01) | |
| *B01J 35/00* | (2006.01) | |
| *B01J 38/02* | (2006.01) | |

(52) U.S. Cl.
CPC ............ *B01J 38/04* (2013.01); *B01J 21/063* (2013.01); *B01J 23/462* (2013.01); *B01J 35/008* (2013.01); *B01J 38/02* (2013.01)

(58) Field of Classification Search
CPC ........ B01J 21/063; B01J 23/462; B01J 23/96; B01J 35/008; B01J 38/02; B01J 38/04; B01J 38/14; B01J 38/52; C07C 67/303; C07C 2601/14; Y02P 20/582; Y02P 20/584

See application file for complete search history.

(56) References Cited

U.S. PATENT DOCUMENTS

| | | | |
|---|---|---|---|
| 7,355,084 B2 | 4/2008 | Bottcher et al. | |
| 7,361,714 B2 | 4/2008 | Grass et al. | |
| 8,207,327 B2 | 6/2012 | Van Laar et al. | |
| 8,895,791 B2 | 11/2014 | Henkelmann et al. | |
| 10,501,392 B2 | 12/2019 | Fridag et al. | |
| 10,787,414 B2 | 9/2020 | Boeck et al. | |
| 2021/0179534 A1 | 6/2021 | Schulz et al. | |

FOREIGN PATENT DOCUMENTS

| | | | | |
|---|---|---|---|---|
| BE | 882 279 A | 7/1980 | | |
| EP | 0037137 | * 10/1981 | .............. | B01J 23/96 |
| WO | 02/100536 A1 | 12/2002 | | |
| WO | 03/103830 A1 | 12/2003 | | |
| WO | 2006/136541 A2 | 12/2006 | | |
| WO | 2008/015103 A2 | 2/2008 | | |

OTHER PUBLICATIONS

Machine Translation of Boettcher et al (WO 02/100536). (Year: 2002).*
Machine Translation of Maisin et la (EP 0037137). (Year: 1981).*
Anton et al., U.S. Appl. No. 17/547,330, filed Dec. 10, 2021.
European Search Report dated Jun. 7, 2021 in EP 20215551.1 (7 pages).

* cited by examiner

*Primary Examiner* — Brian A McCaig

(74) *Attorney, Agent, or Firm* — Grüneberg and Myers PLLC

(57) ABSTRACT

The invention provides a process for regenerating a catalyst used for the ring hydrogenation of an aromatic species, especially an aromatic ester, wherein a gas stream containing a particular amount of oxygen is used for the regeneration.

21 Claims, No Drawings

PROCESS FOR REGENERATION OF HYDROGENATION CATALYSTS

CROSS REFERENCE TO RELATED APPLICATIONS

This application is a 35 U.S.C. § 119 patent application which claims the benefit of European Application No. 20215551.1 filed Dec. 18, 2020, which is incorporated herein by reference in its entirety.

FIELD

The present invention relates to a process for regenerating a catalyst used for the ring hydrogenation of an aromatic species, especially an aromatic ester, wherein a gas stream containing a particular amount of oxygen is used for the regeneration.

BACKGROUND

The hydrogenation of aromatic species, and especially of aromatic esters, in which the aromatic ring is hydrogenated is known and is also referred to as ring hydrogenation. In such a ring hydrogenation, for example, transition metal-containing catalysts are used. Suitable catalysts are known to those skilled in the art. Corresponding hydrogenation processes are also used on an industrial scale.

With increasing duration of the ring hydrogenation, the catalysts used can lose activity, whether as a result of blocking, loss or poisoning of the active sites of the catalyst. If the loss of activity is too high and/or the hydrogenation process can no longer be operated sufficiently economically, the activity of the catalyst must be increased. This is accomplished by means of a regeneration process in which the catalyst is freed of deposited and adhering matter. It is possible here to calcine the catalyst, in which the deposits are removed at high temperatures (>200° C.), but this can be problematic for particular catalysts or else purely for energy reasons on account of the high temperatures.

Catalysts can alternatively be regenerated by passing a gas stream over them, by which the deposits are entrained and hence removed. Such a process for regeneration of ruthenium catalysts is described, for example, in WO 2008/015103 A1. It is a feature of the regeneration disclosed therein that the catalyst is purged with an inert gas until the catalyst has partly or even completely regained its activity. A reason given for the regenerating action described there with reference to benzene hydrogenation is the removal of water, i.e. the drying of the catalyst.

However, the known process has the problem that the regenerating effect can be too small, especially when not just water has to be removed from the catalyst, or not just water but also other substances that lower the hydrogenation activity are present on the catalyst.

SUMMARY

Accordingly, the problem addressed by the present invention was that of providing processes for regenerating a catalyst used for the ring hydrogenation of an aromatic species, especially an aromatic ester, with which an acceptable activity can be achieved better and more quickly.

DETAILED DESCRIPTION

This problem is solved by the process specified in claim 1. Preferred embodiments are specified in the dependent claims. The process according to the invention is a process for regenerating a catalyst used for the ring hydrogenation of an aromatic species in at least one reactor, wherein the regeneration is conducted

- by passing a gas stream having an oxygen content of 100 ppm, preferably 250 ppm, more preferably 380 ppm to 20,000 ppm, preferably 13,000 ppm, more preferably 9000 ppm, over the catalyst to be regenerated;
- at a temperature of 15 to 170° C., preferably of 25 to 150° C., more preferably of 25 to 120° C., most preferably 25 to 110° C.; and
- without removing the catalyst from the at least one reactor.

The process according to the invention, in which small amounts of oxygen are present in the gas stream, the regeneration medium, can achieve advantageous regeneration of the hydrogenation catalyst. The regeneration improves the catalyst activity, which can be effected even at the low oxygen concentrations according to the present invention. The regeneration described here enables subsequent restarting of the ring hydrogenation, by which the actual products of value are produced, at increased conversions and hence more effective performance. At the same time, the comparatively low oxygen concentration prevents excessively elevated temperatures (possibly even only locally) from occurring in the reactor as a result of oxidation processes, which can damage the catalyst or in the worst case lead to reactor damage.

The ring hydrogenation of aromatic species described here, especially of aromatic esters, is typically conducted in at least one reactor, meaning that the ring hydrogenation can be effected in one or more reactors each containing a suitable catalyst. The inventive regeneration of the catalyst used can be effected in any of the reactors present. In the case of presence of multiple reactors, the regeneration can be effected at different times or simultaneously for each reactor, preference being given to simultaneous regeneration of all catalysts in all the reactors present.

According to the invention, the process is suitable for all catalysts used in the ring hydrogenation of aromatic species, especially of aromatic esters. But the catalyst preferably comprises at least one transition metal on a support material, or consists of at least one transition metal on a support material. However, suitable catalysts are also familiar to the person skilled in the art and can be found, for example, in WO 03/103830 A1.

The transition metal of the catalyst to be regenerated is preferably a metal selected from the group consisting of iron, ruthenium, nickel, rhodium, platinum, palladium and mixtures thereof. Ruthenium is the transition metal for the catalyst used which is particularly preferred in the present invention. The content of transition metal in the catalyst to be regenerated is generally 0.1% to 30% by mass. The ruthenium content, calculated as the metal, is preferably in the range from 0.1% to 10% by mass, especially in the range from 0.3% to 5% by mass, very particularly in the range between 0.4% and 2.5% by mass.

The support material on which the transition metal is present is preferably selected from the group consisting of activated carbon, silicon carbide, aluminium oxide, silicon dioxide, aluminosilicate, titanium dioxide, zirconium dioxide, magnesium oxide, zinc oxide and mixtures thereof. Preferred support materials are aluminium oxide, silicon dioxide, titanium dioxide and mixtures thereof. In addition, these support materials may comprise alkali metals, alkaline earth metals and/or sulfur. In a particularly preferred embodiment of the present invention, the catalyst to be regenerated is an eggshell catalyst.

According to the invention, the regeneration medium used is a gas stream. This gas stream preferably consists of an inert gas and oxygen, with the gas stream having an oxygen content of 100 ppm, preferably 250 ppm, more preferably 380 ppm to 20,000 ppm, preferably 13,000 ppm, more preferably 9000 ppm. The inert gas may be nitrogen, helium, neon, argon, carbon dioxide or a mixture thereof. Particular preference is given to using nitrogen as the inert gas. The gas stream in the regeneration may be guided over the catalyst in the same or in the reverse flow direction, based on the flow direction in the ring hydrogenation, preferably in the same flow direction.

When there are multiple hydrogenation reactors, the regeneration medium may be fed exclusively to the first reactor. In that case, the regeneration medium would also be guided from the first reactor to the downstream reactor(s) in order also to regenerate the catalysts therein. But it is preferable that the regeneration medium is guided to every single reactor when there are multiple reactors. The regeneration medium is thus guided directly to every single reactor and does not first pass through the upstream reactor(s).

According to the claims, the regeneration is conducted at a temperature of 15 to 170° C., preferably of 25 to 150° C., more preferably of 25 to 120° C. What is important in this connection is that there is no burnoff of the catalyst here, where the impurities are removed at high temperatures. The pressure in the regeneration is preferably in the range from 0.5 to 200 bar, preferably 1 to 110 bar.

The time for which the regeneration described in the present context has to be conducted in order to improve the catalyst activity to a sufficient degree depends on various factors. Examples of these factors are the nature and amount of the impurities, the characteristics of the reactors (size, diameter) or the characteristics of the catalyst particles (especially size, shape, surface area, pore structure, metal loading, and penetration depth of the metal in the carrier). In a preferred embodiment of the present invention, the duration of the regeneration is at least 24 hours. If the regeneration is ended too early, it may be the case that the catalyst has to be regenerated again even after relatively brief use in the ring hydrogenation.

The regeneration according to the invention is effected in the case of a catalyst used in the ring hydrogenation of an aromatic species. In a preferred embodiment, the regeneration according to the invention is effected in the case of a catalyst used in the ring hydrogenation of an aromatic ester. The aromatic ester is preferably an ester of a benzenecarboxylic acid, an ester of a benzenedicarboxylic acid, an ester of a benzenetricarboxylic acid or an ester of a benzenetetracarboxylic acid, preferably an ester of benzenedicarboxylic acid or of benzenetricarboxylic acid. These include phthalates, isophthalates, terephthalates and trimellitates. Preference is given to esters of benzenedicarboxylic acid, i.e. phthalates, isophthalates and terephthalates. Among these, preference is given particularly to the C8- to C10-alkyl esters, especially the C8- to C10-alkyl esters of phthalic acid (e.g. dioctyl phthalate, diethylhexyl phthalate, diisononyl phthalate, dipropylheptyl phthalate) or the C8- to C10-alkyl esters of terephthalic acid (e.g. dioctyl terephthalate, diethylhexyl terephthalate, diisononyl terephthalate, dipropylheptyl terephthalate).

The ring hydrogenation is preferably conducted in the liquid phase. The ring hydrogenation can be conducted continuously or batchwise over suspended catalysts or those arranged in piece form in a fixed bed. In the process according to the invention, preference is given to continuous ring hydrogenation over a catalyst in fixed bed form, in which the product/reactant phase is mainly in the liquid state under the reaction conditions. Preference is given to operating the reactor(s) as trickle bed reactor(s) that may be completely or partly flooded.

If the ring hydrogenation is conducted continuously over a catalyst in fixed bed form, it is advantageous to convert the catalyst to the active form prior to the first performance of the ring hydrogenation. After a regeneration, such an activation is not absolutely necessary. The activation can be effected by reduction of the catalyst using hydrogen-containing gases according to a temperature programme. The reduction here can optionally be performed in the presence of a liquid phase that trickles over the catalyst. The liquid phase used here may be a solvent or the hydrogenation product. Given corresponding hydrogenation conditions, it is also possible to dispense with such an activation, since this is also effected under reaction conditions.

Various process variants may be chosen for the ring hydrogenation. It may be performed under adiabatic, polytropic or virtually isothermal conditions, i.e. with a temperature rise of typically less than 10° C., in one or more stages. In the latter case, all reactors, appropriately tubular reactors, may be operated adiabatically or virtually isothermally, or else one or more adiabatically and the others virtually isothermally. It is additionally possible to hydrogenate the aromatic polycarboxylic esters in straight pass or with product recycling. It is also possible that two reactors are present, in which case the first reactor is operated with product recycling and the second reactor in straight pass. Another option is performance of the ring hydrogenation as a trickle bed. The reactor here may also be partly or fully flooded.

The ring hydrogenation may be conducted in cocurrent in the liquid/gas mixed phase or in the liquid phase in triphasic reactors, with the hydrogenation gas distributed in the liquid reactant/product stream in a manner known per se. In the interests of a uniform liquid distribution, of improved removal of heat of reaction and of a high space-time yield, the reactors are preferably operated with high liquid loads of 15 to 120, especially of 25 to 80, $m^3$ per $m^2$ of cross section of the empty reactor and per hour. When a reactor is operated in straight pass, the specific liquid hourly space velocity (LHSV) may assume values between 0.1 and 10 $h^{-1}$.

The ring hydrogenation can be conducted in the absence or preferably in the presence of a solvent. The solvent used may be all liquids that form a homogeneous solution with the reactant and product, are inert under hydrogenation conditions and can be easily removed from the product. The solvent may also be a mixture of two or more substances and may optionally comprise water.

For example, it is possible to use the following substances as solvent: straight-chain or cyclic ethers such as tetrahydrofuran or dioxane and also aliphatic alcohols in which the alkyl radical has 1 to 13 carbon atoms. Alcohols usable with preference are, for example, isopropanol, n-butanol, isobutanol, n-pentanol, 2-ethylhexanol, nonanols, technical nonanol mixtures, decanol, technical decanol mixtures, tridecanols.

When alcohols are used as solvent, it may be appropriate to use that alcohol or that alcohol mixture that would form in the hydrolysis of the product. This rules out by-product formation through transesterification. A further preferred solvent is the hydrogenation product itself.

The use of a solvent allows the aromatic species concentration in the reactor feed to be limited, as a result of which better temperature control in the reactor can be achieved. This can minimize side reactions and accordingly bring about an increase in product yield. The aromatic species content in the reactor feed is preferably between 1% and 35%, especially between 5% and 25%. The desired concentration range in the case of reactors that are operated in loop mode can be adjusted via the circulation rate (ratio of hydrogenation output recycled to reactant).

The ring hydrogenation can be conducted within a pressure range from 20 to 300 bar, preferably 40 to 200 bar. The hydrogenation temperatures are preferably in the range from 60° C. to 200° C., especially in the range from 80° C. to 180° C.

Hydrogenation gases used may be any desired hydrogen-containing gas mixtures that do not contain harmful amounts of catalyst poisons, for example carbon monoxide or hydrogen sulfide.

The inert gas constituents may, for example, be nitrogen or methane. Preference is given to using hydrogen in a purity of greater than 95%, especially greater than 98%.

The invention is elucidated hereinafter by examples. These examples disclose exemplary embodiments and should not be regarded as limiting.

Example 1—Equal Oxygen Concentration

For the present experiments, it was first necessary to reproducibly produce a catalyst that was then to be regenerated. In the present case, for this purpose, diisononyl terephthalate (DINT) was hydrogenated continuously. The ring hydrogenation of DINT was effected in a tubular reactor in circulating operation. There was cocurrent flow of liquid phase (DINT and hydrogenation product) and gas phase (hydrogen) in the trickle bed of the tubular circulation reactor. The hydrogenation catalyst used in Example 1 was a commercial ruthenium catalyst (Specialyst® 102: 1% Ru on a $TiO_2$ support, from Evonik Operations GmbH). This was diluted in an equivalent amount with inert material ($TiO_2$) and used in the tubular reactor having an internal diameter of 40 mm and a length of 378 mm. The feed rate of DINT used in the ring hydrogenation was a constant 130 g/h; the circulation flow rate was 80 l/h. The $H_2$ level was under closed-loop control by means of a constant offgas mode with an offgas flow rate of 0.5 l/h. The experiments were each conducted at a system pressure of 100 bar and a tubular reactor temperature of 110° C. The DINT concentration was detected by means of inline Raman analysis. The DINT conversion decreased continuously with time. After about 3700 to 5700 hours, a regeneration was then undertaken in each case.

Prior to the regeneration, the circulation pump and the feed of the reactants were stopped, and the liquids were let out of the circulation reactor. Subsequently, the respective regeneration conditions (e.g. pressure, temperature) were established and the regeneration was conducted for a particular period of time (see Table 1). After the regeneration, circulation pump and the feed of the reactants were restarted in order to conduct a ring hydrogenation again, as described in the previous paragraph. The basis used for the assessment of the effectiveness of the regeneration was sampling immediately before shutdown of the reactant feed (DINT conversion before regeneration) and about 20 to 40 h after restarting of the reactant feed (DINT conversion after regeneration). The results are listed in Table 1 below.

TABLE 1

Experimental data for Example 1

| Regen-eration | Pressure/bar | Time/days | $O_2$ concen-tration/ppm | Circulation reactor conversion/% | | |
|---|---|---|---|---|---|---|
| | | | | Before | After | Difference |
| 1 | 100 | 110 | 3 | 400 | 91.0 | 94.3 | 3.3 |
| 2 | 10 | 110 | 3 | 400 | 90.6 | 94.1 | 3.5 |
| 3 | 10 | 110 | 1 | 400 | 90.8 | 93.9 | 3.1 |

It is apparent from Table 1 that neither the pressure nor the duration of the regeneration has a significant influence on the regeneration.

Example 2—Different Oxygen Concentrations

The experiments for Example 2 were conducted in a similar manner to the experiments for Example 1. All that are detailed hereinafter are therefore the differences from the process in Example 1. The hydrogenation catalyst used was a ruthenium catalyst with a greater amount of Ru (2% Ru on $TiO_2$ support). The feed rate of DINT used in the ring hydrogenation was always 180 g/h, and hydrogenation was effected at a temperature of 92.5° C. By contrast with Example 1, as well as temperature and pressure, the oxygen concentrations in the regeneration were also varied here. For avoidance of problems (with explosive gas mixtures), the reactor was first inertized with $N_2$ prior to the regeneration experiments with relatively high $O_2$ concentration. The results are shown in Table 2.

TABLE 2

Experimental data for Example 2

| Regen-eration | Pressure/bar | Time/days | $O_2$ concen-tration/ppm | Circulation reactor conversion/% | | |
|---|---|---|---|---|---|---|
| | | | | Before | After | Difference |
| 1 | 100 | 110 | 3 | 400 | 90 | 92.5 | 2.5 |
| 2* | 10 | 110 | 4 | 36 | 89.4 | 89.8 | 0.4 |
| 3 | 1 | RT | 1 | 20 000 | 88.2 | 90.2 | 2 |
| 4 | 100 | RT | 1 | 20 000 | 88.5 | 90.6 | 2.1 |
| 5 | 1 | 110 | 1 | 5000 | 88.1 | 91.0 | 2.9 |
| 6 | 100 | RT | 1 | 5000 | 86.8 | 88.7 | 1.9 |

*non-inventive

It is apparent from Table 2 that poorer regenerations were achieved at very low oxygen concentrations. At high oxygen concentrations, regeneration is also better within a short period of time, but it should be noted here that there is the risk of calcination or burnoff of the catalyst at such high concentrations, and it was therefore possible to use only low temperatures or a relatively low pressure. Even higher oxygen concentrations (>20,000 ppm) were found to be unproductive in the present case for safety reasons.

The invention claimed is:
1. A process for regenerating a catalyst used for the ring hydrogenation of an aromatic species in at least one reactor, wherein the regeneration is conducted
by passing a gas stream having an oxygen content of 100 ppm to 9,000 ppm over the catalyst to be regenerated;
at a temperature of from 15 to 170° C.; and
without removing the catalyst from the at least one reactor.

2. The process according to claim 1, wherein the gas stream has an oxygen content of from 250 ppm to 9,000 ppm.

3. The process according to claim 2, wherein the regeneration is conducted at a temperature of from 25° C. to 150° C.

4. The process according to claim 2, wherein the catalyst comprises at least one transition metal on a support material.

5. The process according to claim 2, wherein the gas stream is an inert gas.

6. The process according to claim 1, wherein the gas stream has an oxygen content of from 380 ppm to 9000 ppm.

7. The process according to claim 1, wherein the regeneration is conducted at a temperature of from 25° C. to 150° C.

8. The process according to claim 1, wherein the catalyst comprises at least one transition metal on a support material.

9. The process according to claim 5, wherein the at least one transition metal is a metal selected from the group consisting of iron, ruthenium, nickel, rhodium, platinum, palladium and mixtures thereof.

10. The process according to claim 8, wherein the support material is selected from the group consisting of activated carbon, silicon carbide, aluminium oxide, silicon dioxide, aluminosilicate, titanium dioxide, zirconium dioxide, magnesium oxide, zinc oxide and mixtures thereof.

11. The process according to claim 8, wherein the catalyst used is an eggshell catalyst.

12. The process according to claim 1, wherein the gas stream is an inert gas selected from the group consisting of nitrogen, helium, neon, argon, carbon dioxide and mixtures thereof.

13. The process according to claim 1, wherein the aromatic species is an aromatic ester.

14. The process according to claim 13, wherein the aromatic ester is an ester of a benzenecarboxylic acid, of a benzenedicarboxylic acid, of a benzenetricarboxylic acid or of a benzenetetracarboxylic acid.

15. The process according to claim 14, wherein the aromatic ester is a C8- to C10-alkyl ester of phthalic acid or a C8- to C10-alkyl ester of terephthalic acid.

16. The process according to claim 10, wherein the aromatic ester is an ester of benzenedicarboxylic acid or of benzenetricarboxylic acid.

17. The process according to claim 10, wherein the aromatic ester is an ester of benzenedicarboxylic acid.

18. The process according to claim 1, wherein the regeneration is conducted at a pressure in the range from 0.5 to 200 bar.

19. The process according to claim 1, wherein the duration of the regeneration is at least 24 hours.

20. The process according to claim 1, wherein the gas stream in the regeneration is guided over the catalyst in the same flow direction, based on the flow direction in the hydrogenation.

21. The process according to claim 1, wherein the gas stream in the regeneration is guided over the catalyst in the reverse flow direction, based on the flow direction in the hydrogenation.

* * * * *